(12) United States Patent
Chappo et al.

(10) Patent No.: US 6,917,664 B2
(45) Date of Patent: Jul. 12, 2005

(54) SYMMETRICAL MULTIPLE-SLICE COMPUTED TOMOGRAPHY DATA MANAGEMENT SYSTEM

(75) Inventors: Marc A. Chappo, Elyria, OH (US); Randall P. Luhta, Highland Heights, OH (US); William J. Brunnett, Concord, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 279 days.

(21) Appl. No.: 10/264,238

(22) Filed: Oct. 3, 2002

(65) Prior Publication Data

US 2004/0065465 A1 Apr. 8, 2004

(51) Int. Cl.$^7$ .......................... A61B 6/03; G01N 23/083
(52) U.S. Cl. ........................................ 378/19; 378/15
(58) Field of Search ............................. 378/19, 15

(56) References Cited

U.S. PATENT DOCUMENTS

| | | | | |
|---|---|---|---|---|
| 5,473,663 A | * | 12/1995 | Hsieh | 378/207 |
| 5,991,358 A | | 11/1999 | Dolazza et al. | 378/19 |
| 6,246,743 B1 | | 6/2001 | Kopp, III et al. | 378/19 |
| 6,337,896 B1 | | 1/2002 | Munier et al. | 378/17 |
| 6,415,013 B1 | * | 7/2002 | Hsieh et al. | 378/19 |
| 2002/0085665 A1 | | 7/2002 | Hoffman et al. | 378/19 |
| 2002/0110216 A1 | * | 8/2002 | Saito et al. | 378/19 |
| 2002/0122127 A1 | | 9/2002 | Hoffman | 348/302 |
| 2004/0264633 A1 | * | 12/2004 | Kamimura et al. | 378/19 |

FOREIGN PATENT DOCUMENTS

JP        2001194461        7/2001

* cited by examiner

Primary Examiner—David V. Bruce
Assistant Examiner—Krystyna Suchecki
(74) Attorney, Agent, or Firm—Fay, Sharpe, Fagan, Minnich & McKee LLP

(57) ABSTRACT

A data measurement system (DMS) (30) for a computed tomography (CT) scanner (12) includes a plurality of connectorized detector sub-array modules (32). Each detector sub-array module (32) includes: a scintillator (40) that produces scintillation events responsive to irradiation by x-rays; a photodetector array (42) arranged to detect the scintillations; and two symmetrically arranged signal connectors ($54_1$, $54_2$) that transmit the photodetector signals. Symmetrically mounted pipeline cards (60) mate with the signal connectors (54) of each side of groups of the detector sub-array modules (32) to receive the photodetector signals. A processor (64) communicating with the pipeline cards (60) receives the photodetector signals from the pipeline cards (60) and constructs a DMS output from the photodetector signals.

42 Claims, 10 Drawing Sheets

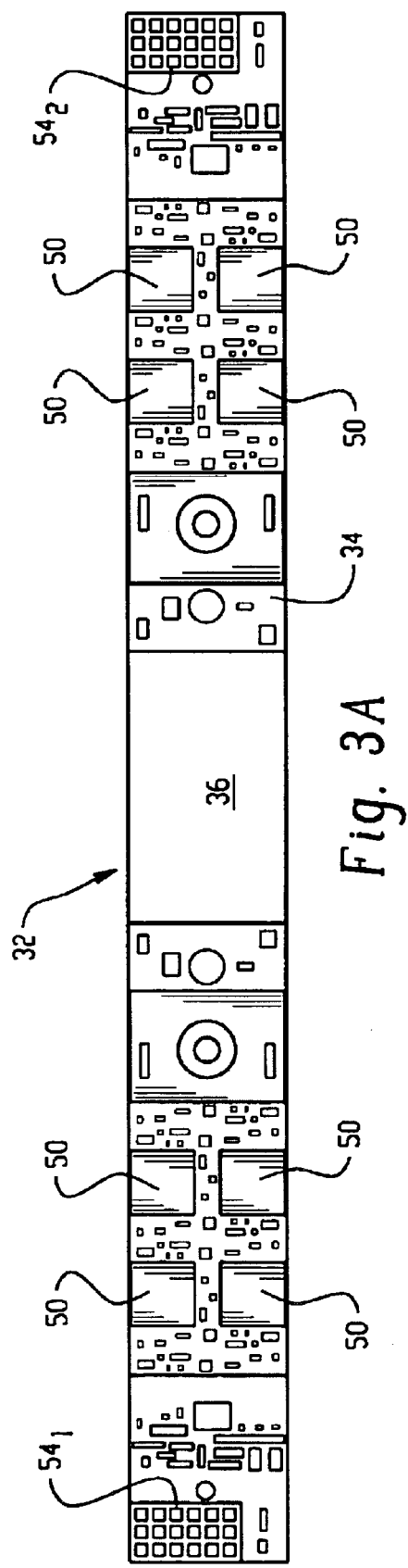
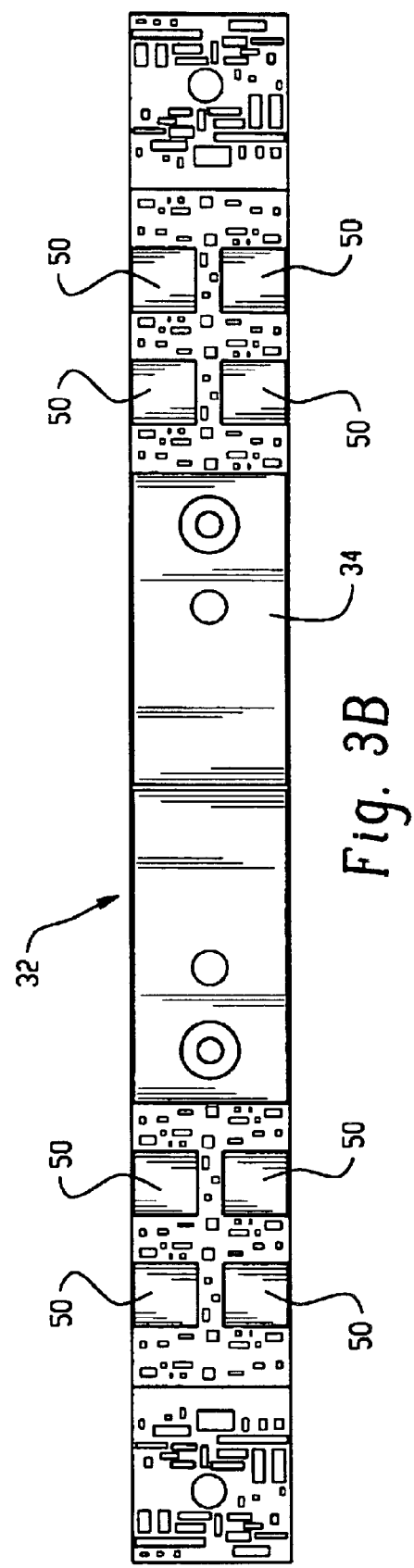
Fig. 3A
Fig. 3B

SYMMETRICAL MULTIPLE-SLICE COMPUTED TOMOGRAPHY DATA MANAGEMENT SYSTEM

BACKGROUND OF THE INVENTION

The present invention relates to the diagnostic imaging arts. It particularly relates to computed tomography imaging employing a two-dimensional detector array that enables rapid acquisition of volumetric imaging data, and will be described with particular reference thereto. However, the invention will also find application in other types of radiation detectors for a variety of imaging applications employing x-rays, visible light, or other types of radiation. The invention will further find application in non-imaging radiation detectors for radiological applications and the like.

Computed tomography (CT) imaging typically employs an x-ray source that generates a fan-beam or cone-beam of x-rays that traverse an examination region. A subject arranged in the examination region interacts with and absorbs a portion of the traversing x-rays. A CT data measurement system (DMS) including a two-dimensional detector array in a cast frame assembly is arranged opposite the x-ray source to detect and measure intensities of the transmitted x-rays. Typically, the x-ray source and the DMS are mounted at opposite sides of a rotating gantry such that the gantry is rotated to obtain an angular range of projection views of the subject.

In helical CT imaging, the patient is advanced linearly through the examination region along a direction that is perpendicular to the gantry rotation plane to effectuate a helical orbiting of the x-ray source about the subject. X-ray absorption data obtained during the helical orbiting is reconstructed using filtered backprojection or another reconstruction method to generate a three-dimensional image representation of the subject or of a selected portion thereof.

The two-dimensional detector array of the DMS typically includes a scintillator crystal or array of scintillators which produce bursts of light, called scintillation events, responsive to impingement of x-rays onto the scintillator. A two-dimensional array of photodetectors such as photodiodes or photomultiplier tubes are arranged to view the scintillator and produce analog electrical signals corresponding to the scintillation events. Preferably, an anti-scattering module is precisely aligned and mounted in front of the scintillator to block scattered x-rays which contribute to measurement noise.

The analog electrical signals are routed via electrical cabling to a remote analog-to-digital converter which digitizes the analog signals. The digitized signals are multiplexed into a reduced number of transmission channels, and the transmission channels communicate the multiplexed digitized signals across the rotating gantry interface by a slipring arrangement.

DMS modules for CT imaging in the past have had a number of deficiencies relating to bulkiness and excessive mass, complex and non-standardized electrical wiring, parasitic noise coupling, complex and difficult optical alignment, and overall system complexity.

The anti-scatter module and the photodetector array must be closely aligned relative to one another and relative to the CT gantry. To achieve the required tolerances, in a conventional DMS the anti-scatter module, the scintillator, and the photodiode array are mechanically isolated from other components of the DMS and mechanically interconnected as a non-detachable captive assembly. Electrical coupling to the photodetector array is obtained by flexible electrical cabling that mechanically decouples the precisely aligned optics from other DMS components.

The amount of electrical cabling involved is substantial. An exemplary DMS having thirty-two rows of detectors (corresponding to thirty-two slices) and 672 detectors per row includes 21,504 detectors, each of which has its own electrical wiring which is brought together at an electronic signal processing module located remotely from the photodetector arrays.

Furthermore, there are many constraints on the arrangement of the electrical cabling. In addition to spatial limitations on and near the rotating gantry, the electrical cabling is further constrained by electrical path length requirements. Differences in the signal path lengths for transmitting the various detector outputs give rise to signal phase differences, data errors, different amounts of transmission noise, and signal delays due to differential signal transit times along paths of different lengths. The analog signals are also susceptible to parasitic noise pick-up if the cabling runs close to electrically active components including the DMS electronics and the x-ray source.

These factors typically lead to electrical routing which is unique for a particular CT scanner. To reduce bulkiness of the DMS due to the cabling, the electrical routing is typically taken off only one side of the DMS. This asymmetrical arrangement leads to signal path length differences. The asymmetrical arrangement can also lead to asymmetries in detector cooling which is corrected using dedicated heaters and fans to distribute heat over the photodetector arrays.

The lack of modularity of conventional DMS modules can also lead to unnecessary component replacement. For example, the captive anti-scatter module and scintillator are typically replaced along with the associated detector array, even though only the detector array may be malfunctioning.

The conventional DMS is typically heavy and bulky, as it includes a cast aluminum frame which supports separate substrates for the photodetectors (usually ceramic) and the remote electronic signal processing circuitry (usually arranged on printed circuit boards), massive quantities of cabling between the detector arrays and the signal processing circuitry, dedicated heaters and fans for temperature control, and electromagnetic shielding to reduce parasitic noise coupling onto the extensive electrical cabling.

The DMS weight and piecemeal construction also places limits on the attainable rotational speed of the gantry and on the data throughput, which in turn limit overall scan speed and the number of views per revolution. The complexity of conventional DMS modules impacts reliability and frequently necessitates field servicing by trained personnel for routine maintenance operations such as replacing and realigning detector array elements.

The present invention contemplates an improved apparatus and method that overcomes the aforementioned limitations and others.

SUMMARY OF THE INVENTION

According to one aspect of the invention, a data measurement system for a computed tomography scanner is disclosed. A plurality of connectorized detector sub-array modules each include: a scintillator that produces scintillation events responsive to irradiation by x-rays; a photodetector array arranged to detect the scintillations; signal conversion ASICs which digitize photodetector signals; and a signal connector that transmits the digitized photodetector signals.

A pipeline card mates with the signal connectors of the detector sub-array modules to receive the photodetector signals. A processor communicating with the pipeline card receives the photodetector signals from the pipeline card. The processor constructs a data measurement system output from the photodetector signals.

According to another aspect of the invention, a computed tomography method is provided for imaging a subject. X-rays are transmitted through the subject. Transmitted x-rays are converted into analog electrical signals over a two-dimensional spatial surface. The analog electrical signals are digitized into digital signals. The digital signals are communicated to a central location via paired communication paths arranged symmetrically about the two-dimensional spatial surface. The digital signals arriving at the central location are stored. The steps of transmitting the x-rays, converting to analog electrical signals, digitizing, communicating via the paired communication paths, and storing are repeated for a plurality of orientations of the two-dimensional spatial surface. The stored digital signals are reconstructed to generate an image representation of the subject.

According to yet another aspect of the invention, a data measurement system for a computed tomography scanner is disclosed. A mechanical frame has four symmetric quadrants defined by first and second planes of symmetry. A plurality of detector sub-array modules each include an x-ray detector sub-array. Each detector sub-array module is arranged symmetrically about the first plane of symmetry. The plurality of sub-array modules are distributed across the mechanical frame symmetrically about the second plane of symmetry. Four pipeline cards are symmetrically arranged in the four symmetric quadrants. Each detector sub-array module electrically communicates with two pipeline cards. A processor is arranged at an intersection of the first and second planes of symmetry. The processor communicates with the pipeline cards to receive signals produced by the x-ray detector sub-arrays of the detector sub-array modules, and processes the received signals for transmission off a rotating gantry on which the data measurement system is mounted.

One advantage of the present invention resides in a symmetric DMS configuration that reduces parasitic noise and provides for a more compact DMS.

Another advantage of the present invention resides in replacement of expensive, bulky, and high mass wiring with printed circuit board signal transmission.

Another advantage of the present invention resides in elimination of expensive cooling and capital equipment.

Another advantage of the present invention resides in improved thermal management.

Another advantage of the present invention resides in reduced mass.

Yet another advantage of the present invention resides in simplification of DMS component alignment within the DMS and with respect to the CT scanner.

Still yet another advantage of the present invention resides in early digitizing of the signals which reduces parasitic noise and permits multiplexing of the signals to reduce the number of transmission channels.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

FIG. 3A shows a detector-side or front-side view of the connectorized detector sub-array module.

FIG. 3B shows a back-side view of the connectorized detector sub-array module.

DETAILED DESCRIPTION OF THE PREFERRED EMBODIMENTS

Figure 1:
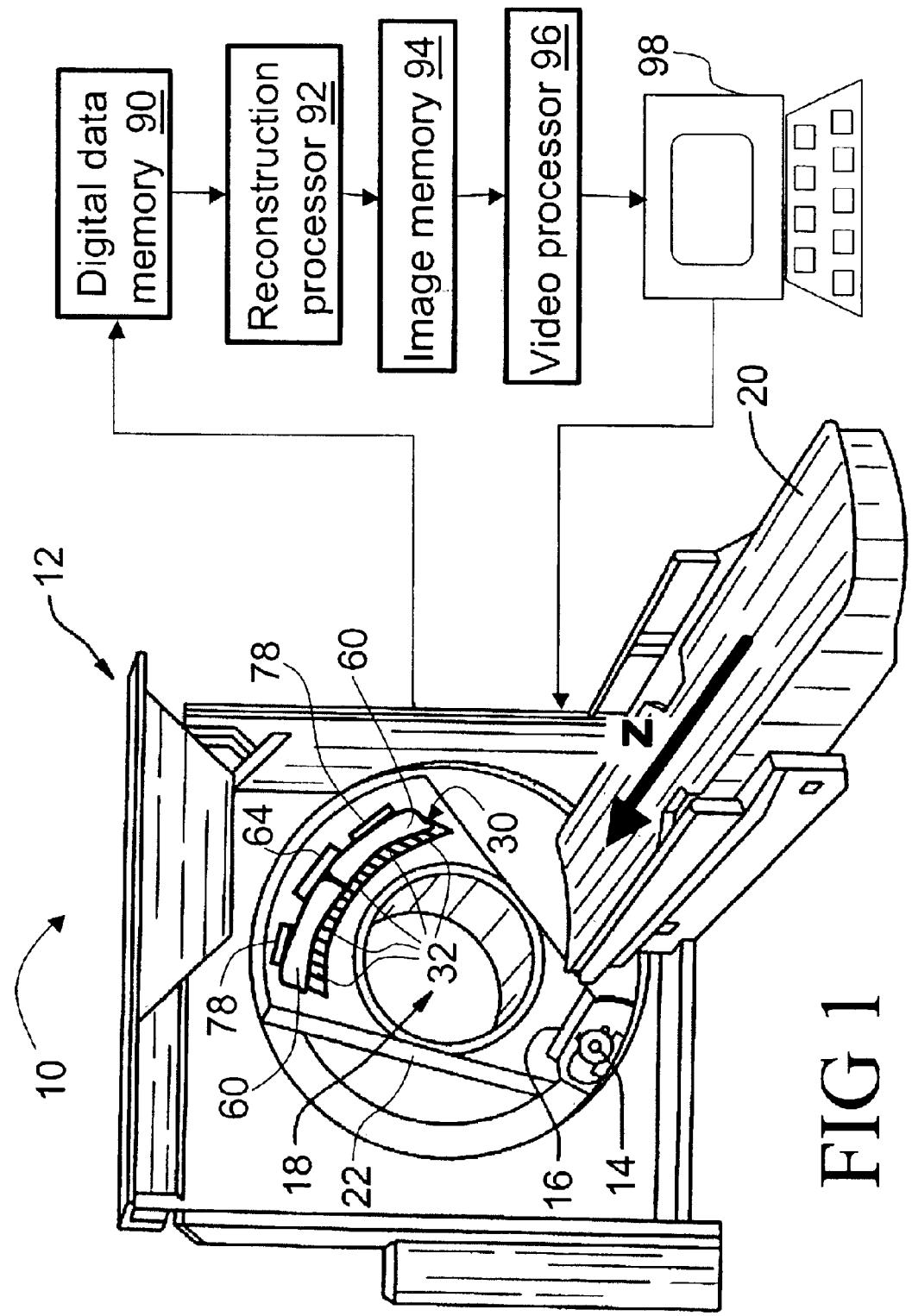
FIG. 1 schematically shows an exemplary computed tomography imaging apparatus according to one embodiment of the invention.

With reference to FIG. 1, a computed tomography (CT) imaging apparatus 10 includes a CT scanner 12 includes an x-ray source 14 and a collimator 16 that cooperate to produce a fan-shaped, cone-shaped, wedge-shaped, or otherwise-shaped x-ray beam directed into an examination region 18 which contains a subject (not shown) such as a patient arranged on a subject support 20. The patient support 20 is linearly movable in a Z-direction while the x-ray source 14 is rotatable on a rotating gantry 22.

In an exemplary helical imaging mode, the gantry 22 rotates simultaneously with linear advancement of the subject support 20 to effectuate a helical orbiting of the x-ray source 14 and collimator 16 about the examination region 18. However, other imaging modes can also be employed, such as a single- or multi-slice imaging mode in which the gantry 22 rotates as the subject support 20 remains stationary to effectuate a circular orbiting of the x-ray source 14 to acquire one or more axial images. After an axial scan is complete, the subject support optionally steps a predetermined distance in the is Z-direction and the circular orbiting is repeated to acquire volumetric data along the Z-direction.

A data measurement system (DMS) 30 is arranged on the gantry 22 across from the x-ray source 14. In the exemplary CT scanner 12, the DMS 30 spans a selected angular range and includes several rows of detectors for acquiring a plurality of image slices simultaneously. The DMS 30 is arranged on the gantry 22 opposite to the x-ray source 14 and rotating therewith so that the DMS receives x-rays that traverse the examination region 14 as the gantry 22 rotates.

Instead of the arrangement shown in FIG. 1, it is also contemplated to arrange the DMS off the rotating gantry in a circumferential arrangement (not shown) on the stationary gantry encircling the rotating gantry such that the x-rays continuously impinge upon some portion of the DMS as the x-ray source 14 rotates.

Figure 2:
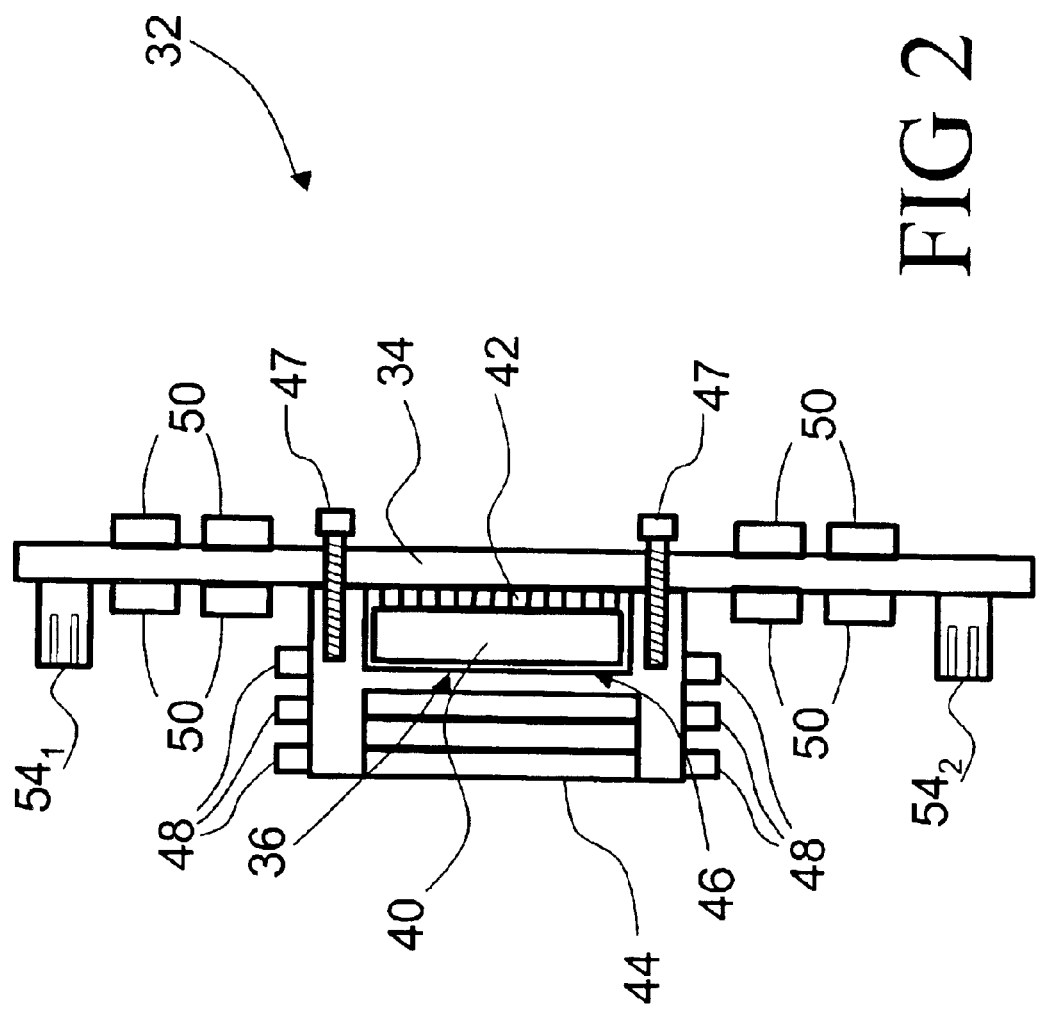
FIG. 2 shows a side view in cross-section of a connectorized detector sub-array module.

With continuing reference to FIG. 1 and with further reference to FIGS. 2, 3A, and 3B, the DMS 30 includes a plurality of connectorized two-dimensional detector sub-array modules 32 arranged to collectively form a DMS detector array that substantially spans a cross-sectional area of the x-ray beam produced by the cooperating x-ray source 14 and collimator 16. Each connectorized detector sub-array module 32 includes a printed circuit board 34 that supports a two-dimensional x-ray detector sub-array 36 arranged generally centered on the circuit board 34. The two-dimensional x-ray detector 36 includes a scintillator crystal 40 and a two-dimensional array of photodetectors 42, e.g. silicon photodiodes, mounted on the circuit board 34 and viewing the scintillator crystal 40. The scintillator crystal 40 is exposed to x-rays produced by the x-ray source 14. An x-ray impingement produces a scintillation event, i.e. a flash of light, which is detected by the photodetector array 42.

With reference to FIG. 2, preferably an anti-scatter plate module 44 is arranged in front of the x-ray detector sub-array 36. As is known to the art, the anti-scatter plate module 44 substantially blocks scattered x-rays that reach the detector sub-array module 32 at large angles from impinging upon the scintillator crystal 40. The anti-scatter plate module 44 suitably interleaves with the scintillator crystal 40, e.g. using a recess 46 in the anti-scatter plate module 44, to provide convenient alignment between the anti-scatter plate module 44 and the photodetector array 42. Pins or threaded fasteners 47 further align and optionally secure together the anti-scatter plate module 44 and the detector sub-array module 32. Preferably, each anti-scatter plate module 44 also includes alignment projections or pins 48 for aligning the anti-scatter plate module 44 within the DMS 30.

Figure 4:
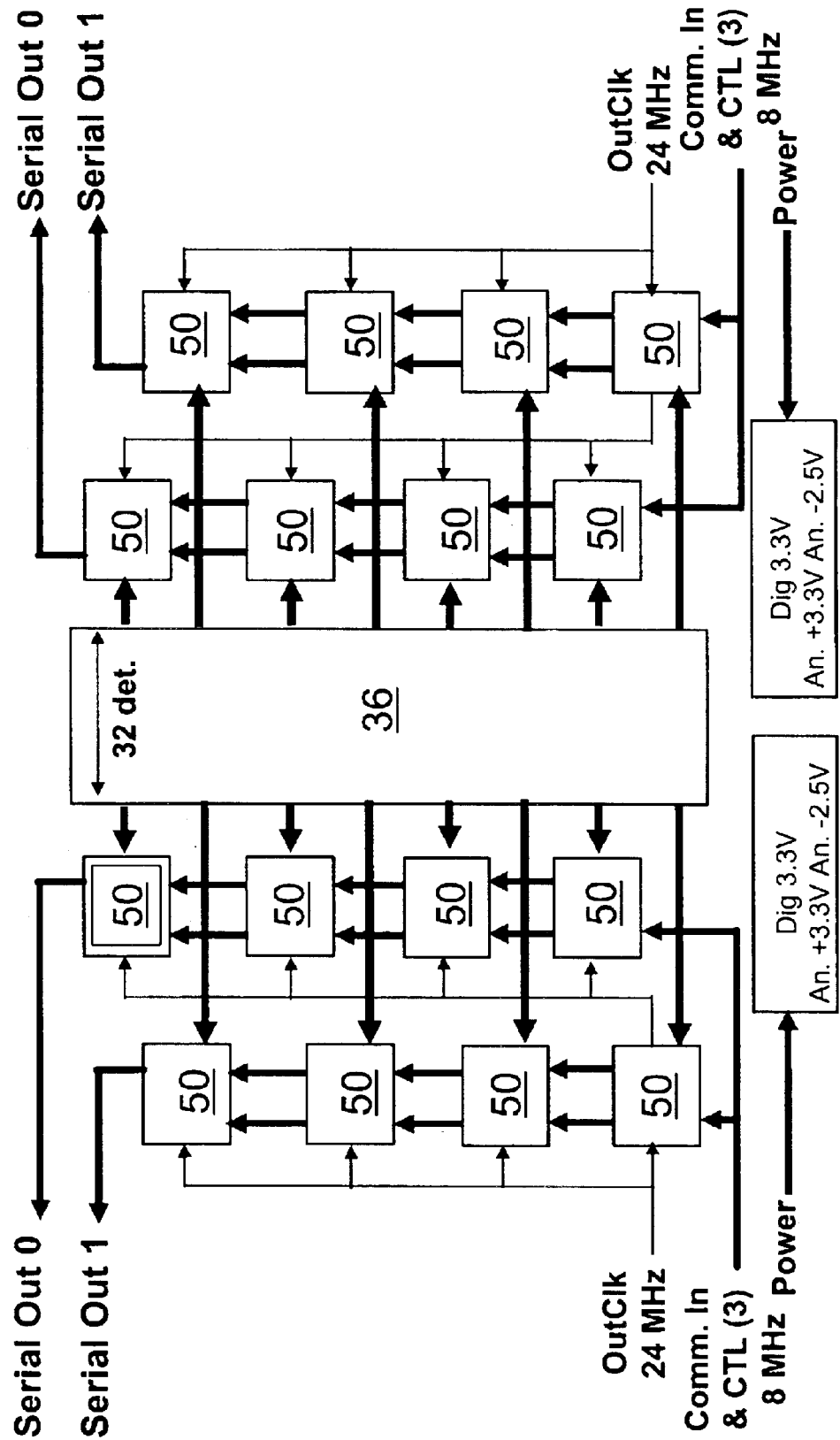
FIG. 4 diagrammatically shows the electrical configuration of the connectorized detector sub-array module of FIGS. 2, 3A, and 3B.

With continuing reference to FIGS. 1–3B and with further reference to FIG. 4, the photodetectors 42 of the x-ray detector sub-array 36 are connected by conductive traces (not shown) on the printed circuit board 34 to application-specific integrated circuits (ASICs) 50 arranged on the front and back of the printed circuit board 34. The ASICs 50 receive electrical output signals of the photodiodes and provide a suitable signal conditioning. In a preferred embodiment, the ASICs 50 perform an analog-to-digital (A/D) conversion of the photodetector signals.

The ASICs 50 are physically arranged in a symmetric fashion around the two-dimensional x-ray detector 36. With reference to FIG. 3A which shows the front or detector side of the connectorized detector sub-array module 32, there are eight ASICs 50 arranged on the front side, with four detectors on each side of the x-ray detector sub-array 36. Similarly, With reference to FIG. 3B which shows the back side of the connectorized detector sub-array module 32, there are eight ASICs 50 arranged on the back side and generally aligned with the positioning of the corresponding ASICs 50 on the front side. This symmetrical arrangement minimizes signal path length differences and parasitic noise coupling.

FIG. 4 diagrammatically shows an exemplary connectorized detector sub-array module 32 with a two-dimensional x-ray detector 36 having a 16×32 element array of photodiodes 42 including 32 detector rows in the slice- or Z-direction and sixteen detectors in each row, i.e. in the circumferential direction of gantry rotation designated herein as the X-direction. The sixteen ASICs 50 are physically and electrically arranged into four symmetric groups of four ASICs 50 each. Each ASIC 50 digitizes thirty-two photodiode signals, and the ASICs in each row digitally communicate to serialize or digitally multiplex the digitized signals. Each group of four ASICs 50 produce a single serial output channel. The serial outputs are communicated to one of connector pairs $54_1$, $54_2$.

The electrical configuration shown in FIG. 4 is exemplary only. Those skilled in the art can select other arrangements for digitizing the photodiode outputs that produce a different number of serial output channels.

It will further be recognized that the digitizing and digital multiplexing of the photodiode outputs early in the signal transmission flow, i.e. on the detector sub-array module 32, has a number of advantages, including elimination of long analog paths which are susceptible to noise coupling, and a reduction in the number of channels taken off the connectorized two-dimensional detector sub-array module 32.

For instance, if the signals are taken off the module 32 in analog form, 512 photodetector channels are needed. In contrast, by employing early digitizing and multiplexing of the serialized data as shown in FIG. 4, four serial output channels can be employed, arranged on the front and back sides of the module 32 symmetrically about the x-ray detector sub-array 36. The symmetry of the connectorized detector sub-array module 32 also affords reliable analog and digital routing paths which result in a high dynamic range data conversion process with reliable high-speed digital data transfer to the connector pair 54.

With particular reference to FIGS. 2 and 3A, each connectorized detector sub-array module 32 includes two connectors $54_1$, $54_2$ symmetrically arranged on the front side of the printed circuit board 34 at opposite sides of the photodetector array 36 and substantially at a periphery of the printed circuit board 34. Each connector 54 of the pair receives and transmits two of the four serialized channels produced by the ASICs 50.

Figure 5:
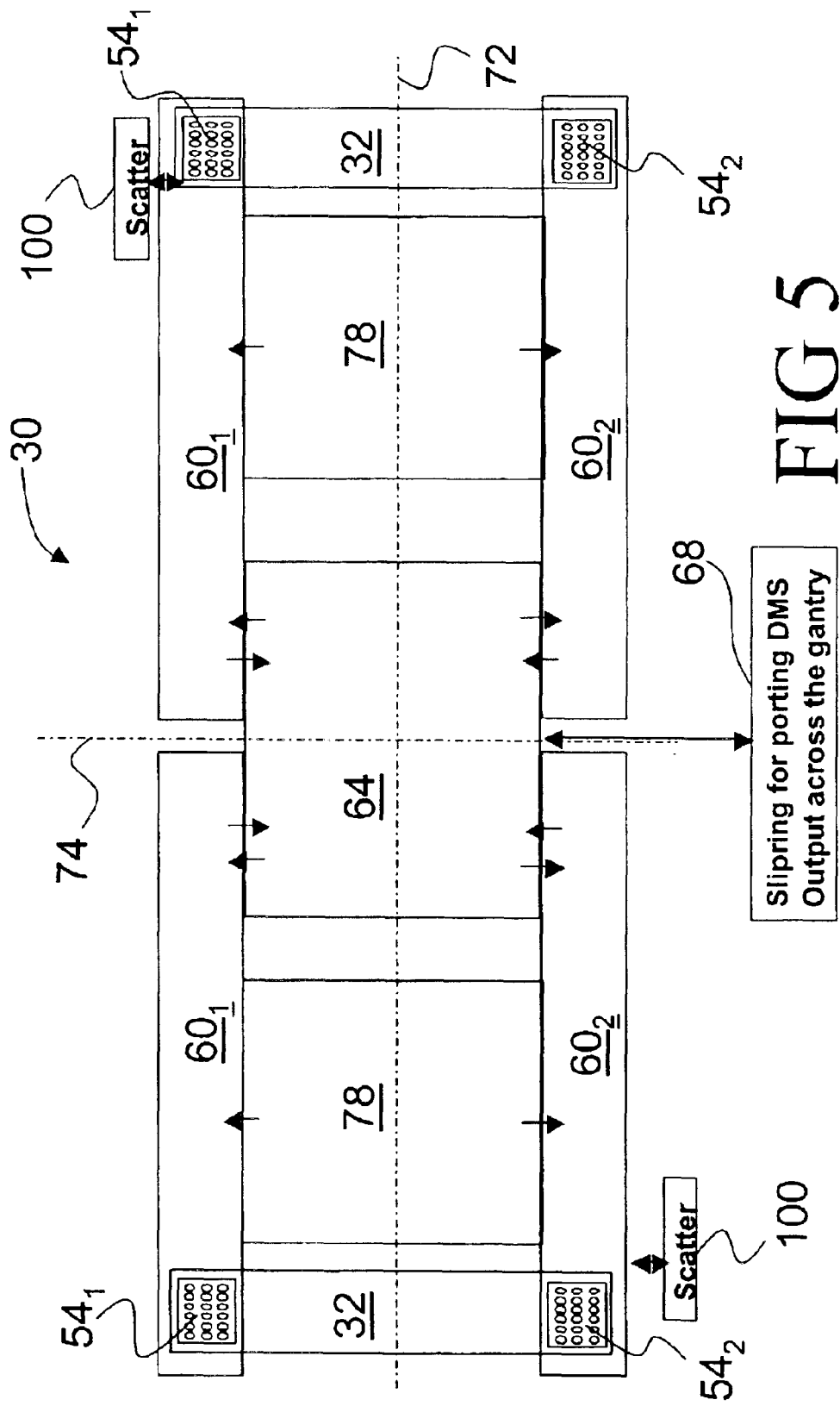
FIG. 5 diagrammatically shows the interconnection and data flow between principle elements of the data measurement system (DMS).

With continuing reference to FIG. 1 and with further reference to FIG. 5, the DMS 30 includes a plurality of connectorized detector sub-array modules 32, e.g. forty-two modules 32 in the exemplary embodiment, of which only the endmost two modules 32 are shown in FIG. 5. Each sub-array module 32 connects with a paired concentrator/pipeline card 60, i.e. two symmetric pipeline cards $60_1$, $60_2$, using the electrical connectors 54. Specifically, the first card $60_1$ connects with the first connector $54_1$ of the sub-array module 32, and the second card $60_2$ connects with the second connector $54_2$.

The concentrator/pipeline card pairs 60 collect the serialized digital photodetector outputs from the plurality of connectorized detector sub-array modules 32 via the connectors 54. The concentrator/pipeline cards 60 are preferably printed circuit boards having suitable digital electronics arranged thereon to perform limited signal processing. The concentrator/pipeline cards 60 further include electrical traces that transmit the processed digital photodetector outputs to a DMS processor 64. The DMS processor 64, which is suitably embodied as a microprocessor, computer, or other integrated circuit, constructs a selected DMS output corresponding to the photodetector signals and transmits the DMS output to a slipring 68 for transmission across the gantry 22.

In the exemplary embodiment, the detector sub-array modules 32 are arranged with the two-dimensional x-ray detectors 36 generally perpendicular to the impinging x-rays, i.e. facing the x-ray source 14. Each concentrator/pipeline card 60₁, 60₂ is generally planar and is orthogonal to the printed circuit boards 34 of the sub-array modules 32 as best seen in FIG. 5. The DMS processor 64 is arranged generally parallel to the printed circuit boards 34 of nearby sub-array modules 32 and behind the modules 32 with respect to the x-ray source 14.

As diagrammatically shown in FIG. 5, the arrangement of the DMS 30 is highly symmetric. Specifically, a biaxial plane of symmetry 72 is defined which generally applies to the concentrator/pipeline card pairs 60, to the connector pairs 54 of the sub-array modules 32, and to the DMS 30 as a whole.

Preferably, the DMS 30 also has a second plane of symmetry 74 arranged perpendicularly to the first plane of symmetry 72. The concentrator/pipeline card pairs 60 include two pairs of concentrator/pipeline cards 60, with the two pairs arranged symmetrically about the second plane of symmetry 74. The two concentrator/pipeline card pairs 60 transmit the digital photodetector signals inward toward the second plane of symmetry 74 where the DMS processor 64 is located generally centered upon an intersection of the first and second planes of symmetry 72, 74.

With continuing reference to FIGS. 1 and 5, two DMS power modules 78 are arranged behind the sub-array modules 32 respective to the x-ray source 14 and generally symmetrically placed with respect to the second plane of symmetry 74. The DMS power modules 78 connect with and supply electrical power to the concentrator/pipeline cards 60. Power conduction traces (not shown) on the concentrator/pipeline cards 60 further distribute the supplied electrical power to the detector sub-array modules 32 and the DMS processor 64.

Preferably, each of the two DMS power modules 78 supply power to one-half of the sub-array modules 32 in a symmetric power distribution arrangement. In FIG. 5 the DMS power module 78 left of the second plane of symmetry 74 powers the elements on the left side of the second plane of symmetry 74, while the DMS power module 78 right of the second plane of symmetry 74 powers the elements on the right side of the second plane of symmetry 74.

With reference to FIGS. 1 and 5, the DMS output crosses the rotating gantry 22 via the sliprng 68 and is communicated to a digital data memory 90 for storage. The gantry 22 and the subject support 20 cooperate to obtain selected projection views of the subject, for example using a helical path of the x-ray source 14 relative to the subject. The path of the x-ray source 14 preferably provides substantial angular coverage for each image slice to minimize image artifacts.

A reconstruction processor 92 reconstructs the acquired projection data, using filtered backprojection or another reconstruction method, to generate a three-dimensional image representation of the subject or of a selected portion thereof which is stored in an image memory 94. The image representation is rendered or otherwise manipulated by a video processor 96 to produce a human-viewable image that is displayed on a graphical user interface (GUI) 98 or another display device, printing device, or the like for viewing by an operator. Optionally, the GUI 98 is also programmed to interface the operator with the CT scanner 12 to allow the operator to initialize, execute, and control CT imaging sessions.

In a suitable exemplary embodiment, the DMS 30 includes forty-two detector sub-array modules 32 each having a 16×32 array of photodiodes 42 (32 slice rows with 16 detectors each). This corresponds to 16×42=672 pixels per slice row, or 672×32=21,504 pixels per projection view. At a 120 rpm gantry rotation rate (i.e., two revolutions per second) and 2320 projection views per revolution, this arrangement outputs at a bit rate of:

$$\text{bit rate} = 21504 \frac{\text{pixels}}{\text{view}} \times 2320 \frac{\text{views}}{\text{rev.}} \times 2 \frac{\text{rev.}}{\text{sec}} \times 16 \frac{\text{bits}}{\text{pixel}} \quad (1)$$

$$= 1.6 \text{ Gbits/sec}$$

where a digitizing of two bytes (i.e., 16 bits) per pixel is used. Accounting for encoding, outputs of scatter detectors 100 (see FIG. 5), and the like, a bit rate of around 2 Gbits/sec is produced by the DMS 30.

Figure 6:
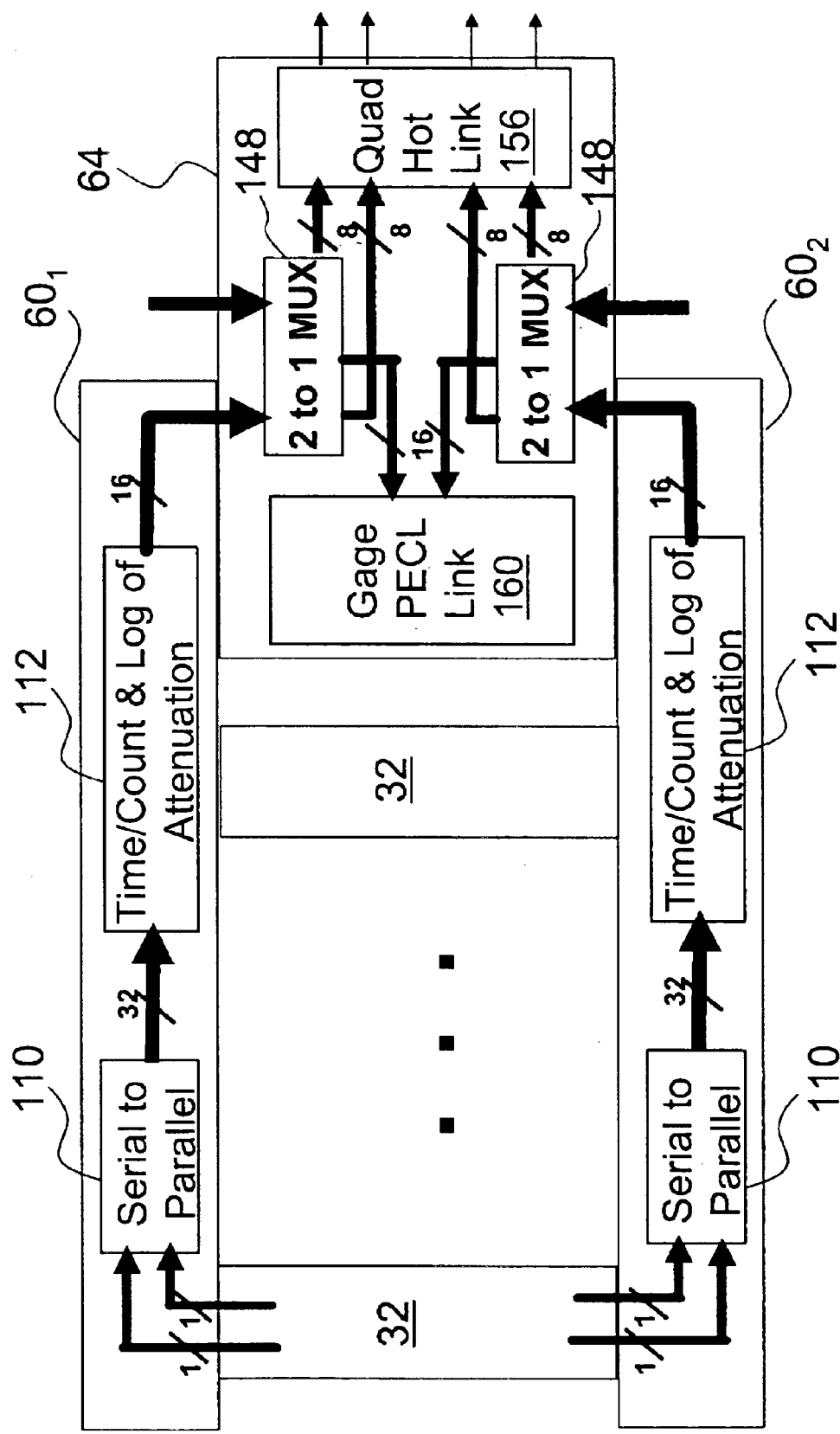
FIG. 6 diagrammatically shows the data flow between the detector sub-array modules, the concentrator/pipeline card pair, and the DMS processor.

With reference to FIG. 6 which diagrammatically shows about half of the DMS 30 (i.e. one side of the second plane of symmetry 74), in a suitable electrical configuration for high-speed data acquisition the sub-array modules 32 each output four serialized digital channels as described previously. The ASICs 50 preferably output the serial data at about 24 MHz to the concentrator/pipeline cards 60 via the connector pairs 54. The concentrator/pipeline cards 60 perform selected manipulations of the digital data en route to the DMS processor 64.

In an exemplary embodiment shown in FIG. 6, the concentrator/pipeline cards 60 perform serial-to-parallel data conversion of the four serialized channels output by each sub-array module 32 to recover the individual photodiode signals in digitized format. The photodiode signals are then converted into a logarithmic attenuation format a by a signal processing block 112. This processing preferably occurs at about 40 MHz.

Figure 7:
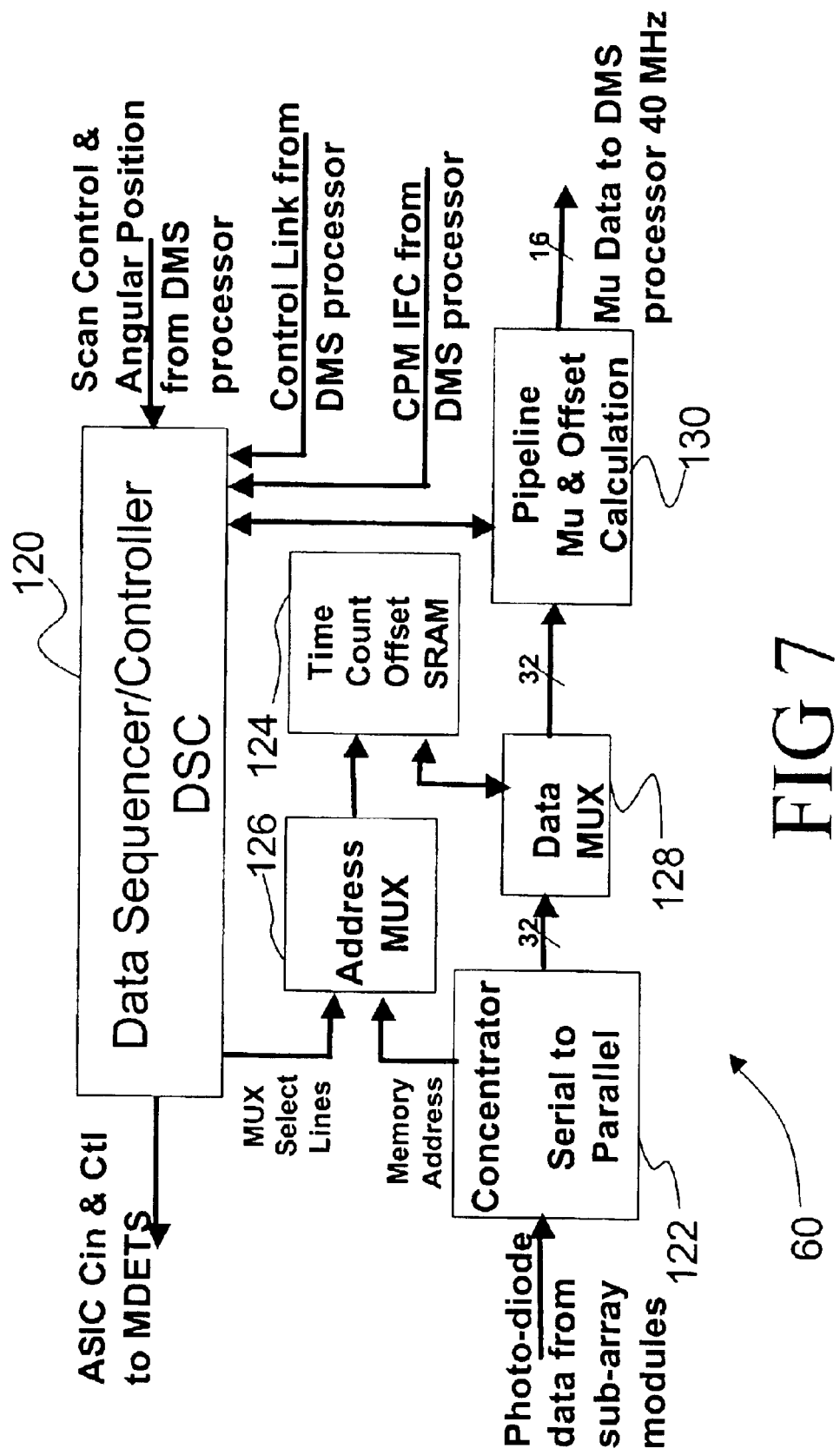
FIG. 7 diagrammatically shows the electrical configuration of the concentrator/pipeline card.

With continuing reference to FIG. 6 and with further reference to FIG. 7, the concentrator/pipeline cards 60 include a data sequencer/controller 120 that communicates timing signals to the connectorized detector sub-array modules 32. The timing signals coordinate the analog-to-digital conversions and the transmission of digitized photodetector signals via the serialized output channels of the sub-array modules 32. The digitized photodetector signals are processed by a concentrator 122, e.g. by a serial-to-parallel conversion, to recover the individual photodiode signals along with associated acquisition timing information. The recovered data is offset-corrected with information contained in an SRAM 124 using multiplexors 126, 128. The offset-corrected count values are divided by time values to produce frequency values proportional to detector currents, and converted to log or "Mu" values in a digital signal processing block 130. The Mu values are transmitted to the DMS processor 64.

The signal processing for the concentrator/pipeline cards 60 just described is exemplary only; those skilled in the art can readily substitute different digital signal processing components to perform the same or different data manipulations. However, it will be recognized that performing extensive signal processing on the concentrator/pipeline cards 60 can impact the data throughput of the concentrator/pipeline card pairs 60 and of the DMS 30 as a whole.

Figure 8:
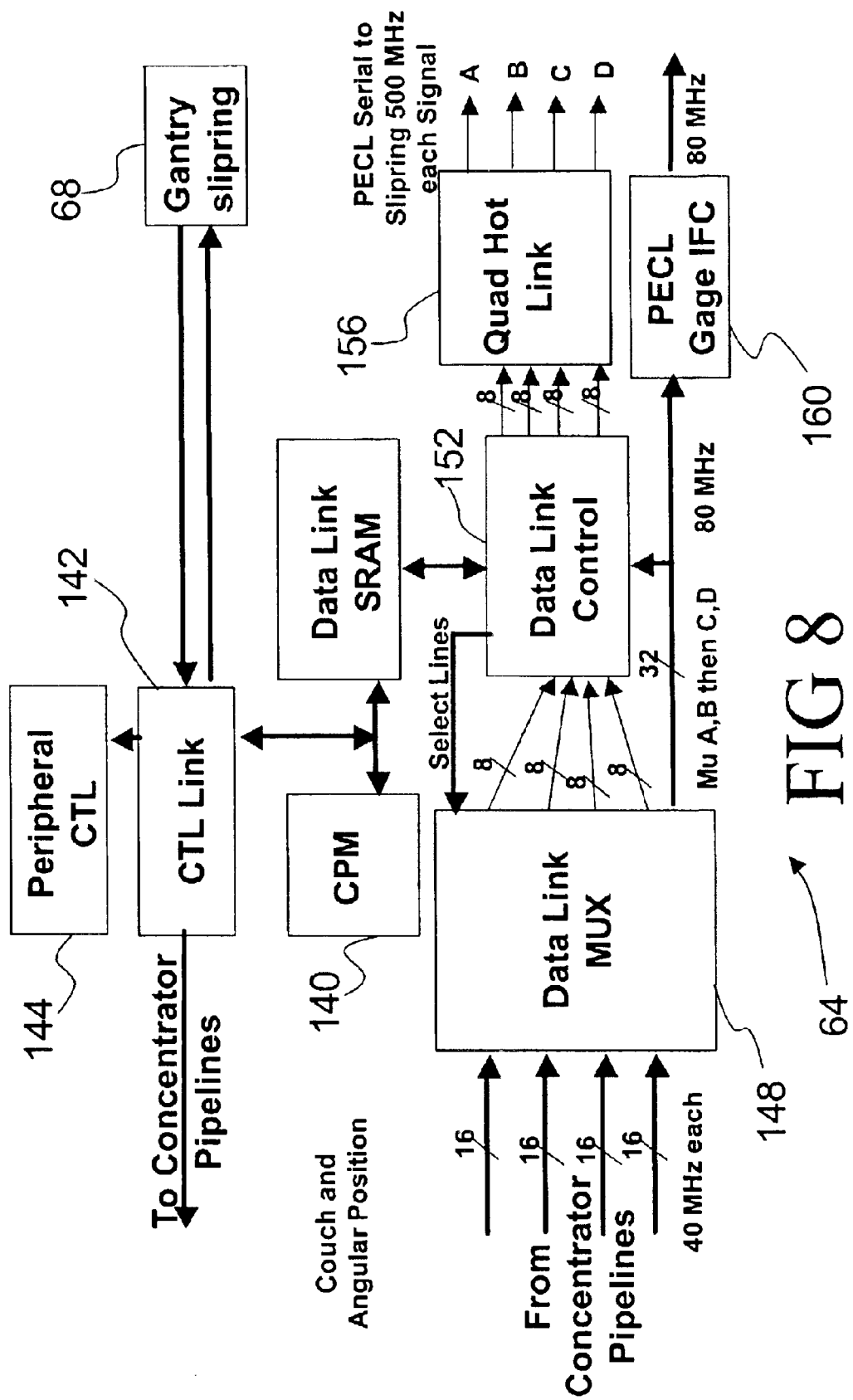
FIG. 8 diagrammatically shows the electrical configuration of the DMS processor.

With continuing reference to FIG. 6 and with further reference to FIG. 8, the DMS processor 64 includes an optional common processor module (CPM) 140 that serves as a master controller for the CT scanner during image data acquisition. The CPM 140 is in direct communication with GUI interface 98 (see FIG. 1) or other off-gantry components via a slipring CAN bus or other high-speed port, and sets up parameters for a scan acquisition on the DMS processor 64. In particular, a high-speed control link 142 sends real-time gantry 22 angular position and patent support 20 position data to the CPM 140 which then coordinates scan acquisitions by setting up the connectorized detector sub-array modules 32 and the concentrator/pipeline card pairs 60. The CPM 140 also sets up and controls other peripherals via a peripheral control module 144.

Although in the exemplary embodiment the DMS processor 64 incorporates master control for the CT scanner 12 via the CPM 140, a CT scanner master controller for controlling the overall operation of the CT scanner is optionally instead located remotely from the DMS, in which case the remote master controller would send control signals to the DMS processor to control the DMS.

During imaging, a multiplexor 148 multiplexes four 16 bit parallel, 40 MHz data streams from the four concentrator/pipeline cards 60 (i.e., two card pairs 60 each including two symmetric cards $60_1$, $60_2$) into one thirty-two bit parallel 80 MHz data stream which is sent via a data link control 152 to a transceiver module 156 which converts the parallel data into one or more high-capacity parallel data streams. In one suitable transceiver module embodiment, a quad HOT-Link® transceiver (available from Cypress Semiconductor Corporation) converts the thirty-two bit parallel data into four serial streams of 500 MHz each. These signals are sent as PECL level differential signals to a slipring interface which transmits them over the slipring 68 optically to the stationary part of the scanner, where another interface then re-transmits them optically over four fiber optic cables to the digital data memory 90.

Although a fiber optical link across the slipring 68 is described, other data porting arrangements can be employed. The data can be transmitted in digitized electrical form across the slipring. It is also contemplated to employ a short-range radio frequency transmitter on the rotating gantry 22 to transmit data off the gantry 22, optionally directly to the data memory 90, without using a slipring.

Optionally, calibration and/or diagnostic electronics 160, such as a PECL Gage IFC, are incorporated into the DMS processor 64 to facilitate maintenance and calibration of the DMS 30. The configuration of the illustrated DMS processor 64 is exemplary only, and those skilled in the art can construct other control and digital signal processing components to perform specific control and data processing tasks for specific DMS modules.

Figure 9:
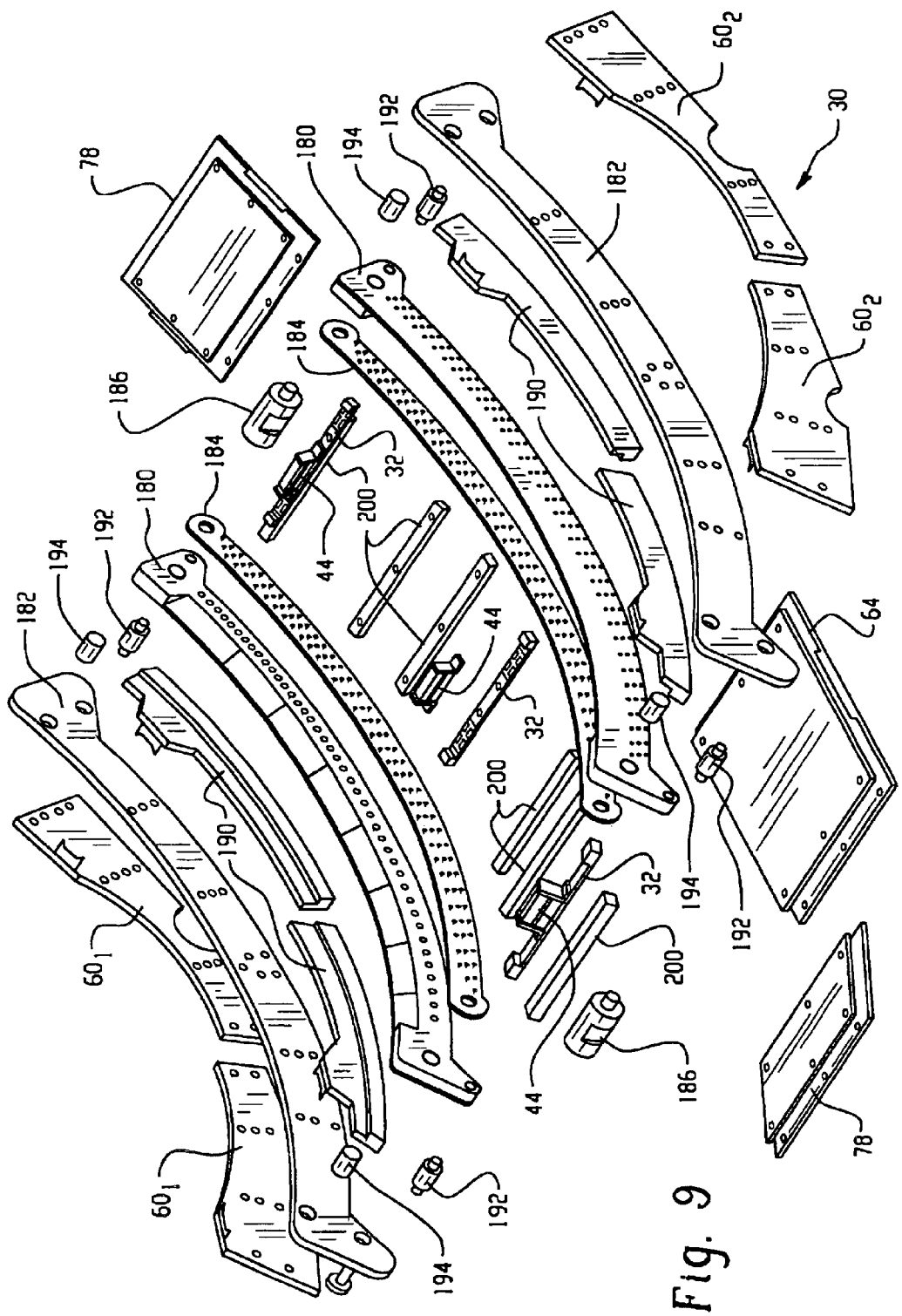
FIG. 9 shows an exploded perspective view of the data management system module with the anti-scatter plate modules and the connectorized detector sub-array modules removed.
Figure 10:
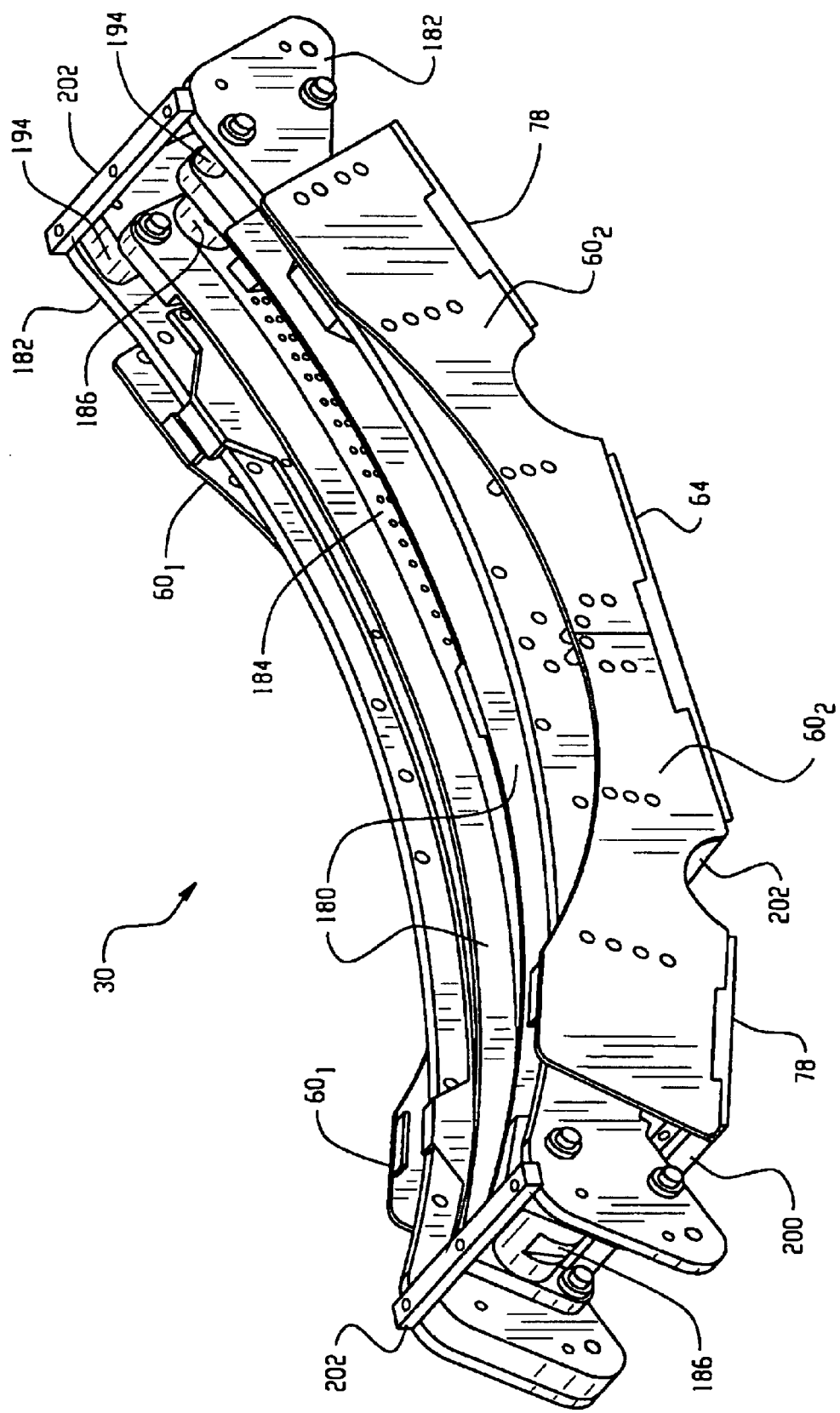
FIG. 10 shows a perspective view of the data management system module, with three exemplary anti-scatter plate module/detector sub-array module assemblies included.

With reference to FIGS. 9 and 10, a suitable method for mechanically constructing the DMS 30 is described. A mechanical DMS frame includes a pair of generally planar, interchangeable inner cradle support elements 180 arranged symmetrically about the first plane of symmetry 72, and a pair of generally planar, interchangeable outer cradle support elements 182 arranged symmetrically about the first plane of symmetry 72 outside of the inner cradle support element pair 180.

Generally planar paired alignment plates 184 are fastened to inner surfaces of the paired inner cradle support elements 180. Inner spacer elements 186 are arranged between the paired inner cradle support element/alignment plate pairs 180, 184 and define a selected spacing between the elements of the inner cradle about the first plane of symmetry 72.

The selected spacing defined by the inner spacer elements 186 defines a gap symmetrically arranged about the first plane of symmetry 72, which gap receives the anti-scatter plate modules 44. The alignment plates 184 include paired alignment openings that receive the projections or pins 48 of the anti-scatter plate modules 44 (see FIG. 2) to align the anti-scatter plate modules 44 within the inner cradle support element pair 180.

Once the inner cradle portion including the anti-scatter plate modules 44 is assembled, a scatter detector assembly is optionally arranged about the inner cradle assembly. Paired scatter detector assemblies 190 are attached to the paired generally planar outer cradle support elements 182. In the arrangement of FIG. 9, the scatter detector assemblies 190 are arranged as quadrant elements, i.e. four scatter detector elements 190 arranged symmetrically about the first and second planes of symmetry 72, 74 analogously to the arrangement of the concentrator/pipeline cards 60 (cf. FIG. 5). The outer cradle support elements 182 are in turn attached to the inner cradle support elements 180 using threaded pin spacers 192 and threaded spacers 194.

The two concentrator/pipeline card pairs 60, i.e. four concentrator/pipeline cards $60_1$, $60_2$, are attached to the outer cradle support elements 182. The connectorized detector sub-array modules 32 plug into the concentrator/pipeline card pairs 60 via the connectors $54_1$, $54_2$ (see FIG. 2). In the illustrated embodiment of FIG. 9, the detector sub-array modules 32 are mechanically secured by connecting the signal connectors 54 to the concentrator/pipeline card pair 60, and are aligned with the anti-scatter plate module 44 by interleaving of the scintillator crystal 40 with the recess 46 of the anti-scatter plate module 44 and by the alignment pins 47 (see FIG. 2). Optionally, each detector sub-array module 32 is further secured to the DMS 30 by using threaded fasteners for the alignment pins 47, or by screws or other supplementary mechanical supports.

Crossing support bars 200, e.g. six support bars 200 in FIG. 9, are attached to and bridge between the concentrator/pipeline card pair elements $60_1$, $60_2$. The DMS processor 64 and the two power modules 78 plug into the concentrator/pipeline card pair elements $60_1$, $60_2$ and are mechanically secured by the support bars 200, e.g. by being fastened thereto by screws or the like. Optionally, the mechanical frame of the DMS 30 further includes additional crossing support elements 202 (see FIG. 10) arranged between the inner and/or outer cradle support elements 180, 182 to provide further mechanical support.

Those skilled in the art will recognize that the DMS assembly just described with particular reference to FIGS. 2, 9, and 10 advantageously does not include the extensive signal cabling typical of other known DMS modules. Furthermore, the DMS 30 has the connectorized detector sub-array modules 32 conveniently arranged for replacement with minimal disassembly of the DMS 30 (e.g., removal of the connectorized DMS processor 64 or power module 78 that blocks access to the target sub-array module 32 and removal of the module 32) and without requiring replacement of the corresponding anti-scatter plate module 44.

The mechanical frame elements, e.g. the inner and outer cradle support elements 180, 182 are suitably manufactured from plate aluminum, while the spacer elements 186, 192, 194 and cross elements 200, 202 are suitably manufactured from stock extrusions. The use of stock materials is a significant advantage over conventional DMS modules whose frames are typically formed from cast metal.

It is also contemplated to omit conventional dedicated heater elements from the DMS 30. Thermal simulations have indicated that the symmetric design of the DMS 30 substantially reduces temperature non-uniformities. These simulations indicate that fan air circulation distributing heat generated by the detector sub-array modules 32, the DMS processor 64, and the DMS power modules 78 should be sufficient to provide substantially a uniform temperature distribution in the DMS 30. The detector sub-array modules 32, the concentrator-pipeline cards 60, the DMS processor 64, and the DMS power modules 78, each optionally include printed circuit board ground planes of copper or another thermally conductive material which provide effective thermal channeling of heat generated by the DMS 30 for efficient, uniform thermal distribution.

The above-described embodiments include multiple structural and electrical symmetries. The overall DMS 30 includes structural and electrical bilateral symmetry about the first plane of symmetry 72, and structural and electrical bilateral symmetry about the second orthogonal plane of symmetry 74. Moreover, each detector sub-array module 32 includes structural symmetry about the centrally positioned x-ray detector 36, with the ASICs 50 and the connectors $54_1$, $54_2$ symmetrically distributed about the detector 36. Each detector sub-array module 32 further includes electrical symmetry in that the electrical signals are transmitted symmetrically with one-half of the signals going to the connector $54_1$ and the other half of the signals going to the connector $54_2$.

These various symmetries each provide benefits, and those skilled in the art can readily relax one or more symmetries of the exemplary DMS 30 or components thereof, while retaining substantial benefits of the remaining symmetries. For example, the x-ray detector module 36 can be positioned off-center along the Z-direction on the sub-array modules 32 for certain asymmetric imaging applications, while maintaining the overall structural and electrical symmetries of the DMS 30 about the first and second planes of symmetry 72, 74, and while substantially retaining the electrical symmetry of the detector sub-array modules 32. Such off-center positioning of the x-ray detector module 36 can be used, for example, to correct for non-uniformities of the x-ray cone.

Moreover, such a change in detector positioning is readily manufactured by modifying only the detector sub-array modules 32. The connectorized construction of the DMS 30 allows the modified sub-array modules to be incorporated into the existing framework of the DMS 30 without additional structural or electrical modifications.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A data measurement system for a computed tomography scanner, the data measurement system comprising:
   a plurality of connectorized detector sub-array modules, each module including a scintillator that produces scintillation events responsive to irradiation by x-rays, a photodetector array arranged to detect the scintillations, and a signal connector that transmits the photodetector signals;
   a pipeline card mating with the signal connectors of the detector sub-array modules to receive the photodetector signals; and
   a processor communicating with the pipeline card to receive the photodetector signals from the pipeline card, the processor constructing a data measurement system output from the photodetector signals.

2. The data measurement system as set forth in claim 1, wherein each connectorized detector sub-array module further includes:
   at least one signal converter including an analog-to-digital conversion element that converts the photodetector signals into digitized photodetector signals, the signal converter communicating the digitized photodetector signals to the signal connector.

3. The data measurement system as set forth in claim 2, wherein the signal converter further includes:
   a serializing element that serially arranges the digitized photodetector signals and communicates the serially arranged photodetector signals to the signal connector.

4. The data measurement system as set forth in claim 3, wherein the pipeline card includes:
   a serial-to-parallel converter that converts the serially arranged photodetector signals into parallel signal channels corresponding to the photodetectors.

5. The data measurement system as set forth in claim 1, wherein the processor further includes:
   a multiplexor that combines the photodetector signals to construct a data measurement system output including one or more multiplexed signals each including a plurality of multiplexed photodetector signals.

6. The data measurement system as set forth in claim 1, further including:
   a plurality of anti-scatter modules corresponding to the plurality of connectorized detector sub-array modules, each anti-scatter module arranged between an examination region of the computed tomography scanner and the corresponding detector sub-array module to substantially reduce noise due to scattered x-rays.

7. The data measurement system as set forth in claim 6, further including:
   alignment pins that align each anti-scatter module with the corresponding connectorized detector sub-array module.

8. The data measurement system as set forth in claim 6, wherein the anti-scatter module interleaves with the scintillator of the connectorized detector sub-array module.

9. The data measurement system as set forth in claim 1, wherein:
   each detector sub-array module signal connector includes a signal connector pair, and the photodetector signals are symmetrically divided between the connectors of the signal connector pair; and
   the pipeline card includes a pipeline card pair that connects with the detector sub-array module signal connector pairs to receive the photodetector signals, the pipeline card pair including a plurality of signal transmission paths divided symmetrically between the two pipeline cards to carry the photodetector signals.

10. The data measurement system as set forth in claim 9, wherein each connectorized detector sub-array module further includes:
    a printed circuit board including electrical traces that communicate photodetector signals to the signal connector pair.

11. The data measurement system as set forth in claim 10, wherein the photodetector array is substantially centered on the printed circuit board, and the connectors of the signal connector pair are arranged at opposite sides of the photodetector array and substantially at a periphery of the printed circuit board.

12. The data measurement system as set forth in claim 11, wherein each connectorized detector sub-array module further includes:
    an even number of analog-to-digital converters arranged symmetrically about the photodetector array on the printed circuit board, wherein signals from one-half of the analog-to-digital converters are transmitted to one connector of the signal connector pair, and signals from the other half of the analog-to-digital converters are transmitted to the other connector of the signal connector pair.

13. The data measurement system as set forth in claim 12, wherein the number of analog-to-digital converters is at least four, and the analog-to-digital converters are symmetrically arranged with one-half of the analog-to-digital converters on a front side of the printed circuit board, and the other half of the analog-to-digital converters on a back side of the printed circuit board.

14. The data measurement system as set forth in claim 10, wherein each connectorized detector sub-array module further includes:

at least one integrated circuit arranged on the circuit board that digitizes the photodetector signals, the digitized photodetector signals being communicated to the signal connector pair.

15. The data measurement system as set forth in claim 10, wherein the photodetector array is arranged off-center along a Z-direction on the printed circuit board and the connectors of the signal connector pair are arranged at opposite sides of the photodetector array and substantially at a periphery of the printed circuit board.

16. The data measurement system as set forth in claim 9, wherein each card of the symmetric pipeline pair further includes:

a printed circuit board on which the plurality of signal transmission paths are arranged as electrical traces.

17. The data measurement system as set forth in claim 9, further including:

a mechanical frame supporting the detector sub-array modules, the symmetric pipeline card pair, and the processor to define a unitary data measurement system that is bilaterally symmetric about a plane of symmetry with each of the detector sub-array module signal connector pairs and the symmetric pipeline card pair arranged symmetrically about the plane of symmetry.

18. The data measurement system as set forth in claim 17, wherein each of the detector sub-array module signal connector pairs and the symmetric pipeline card pair are arranged symmetrically about the plane of symmetry.

19. The data measurement system as set forth in claim 17, wherein the photodetector signal paths are arranged bilaterally symmetrically about the plane of symmetry.

20. The data measurement system as set forth in claim 17, wherein the symmetric pipeline card pair includes two symmetric pipeline card pairs supported by the mechanical frame, the data measurement system having a second plane of symmetry that along with the plane of symmetry defines four detector quadrants, each quadrant including one pipeline card.

21. The data measurement system as set forth in claim 20, further including:

an even number of power modules supported by the mechanical frame that provides electrical power to the detector sub-array modules, the pipeline card pair, and the processor, wherein one-half of the power modules distribute electrical power to a left side of the second plane of symmetry, and the other half of the power modules distribute electrical power to a right side of the second plane of symmetry.

22. The data measurement system as set forth in claim 17, wherein the mechanical frame has a curved shape such that the detector sub-array modules are arranged to interact with x-rays produced by an x-ray source of the computed tomography scanner along a substantially radial surface centered on the x-ray source.

23. The data measurement system as set forth in claim 17, further including:

a power module supported by the mechanical frame that provides electrical power to the detector sub-array modules, the pipeline card pair, and the processor.

24. The data measurement system as set forth in claim 17, wherein the pipeline card pair is supported by the mechanical frame and each detector sub-array module is supported by connections to the pipeline card pair.

25. The data measurement system as set forth in claim 17, further including:

at least one scatter detector pair supported by the mechanical frame, the detectors of the scatter detector pair arranged symmetrically about the plane of symmetry.

26. The data measurement system as set forth in claim 17, wherein the mechanical frame includes:

at least one pair of generally planar support elements symmetrically arranged about the plane of symmetry; and cross elements extending between the elements of the substantially planar support element pair.

27. The data measurement system as set forth in claim 26, wherein the generally planar support elements are constructed from plate metal stock.

28. The data measurement system as set forth in claim 26, wherein the connectorized detector sub-array modules extend between the generally planar support element pair.

29. The data measurement system as set forth in claim 9, wherein the processor mates with the pipeline card pair to receive the photodetector signals from the pipeline card pair.

30. The data measurement system as set forth in claim 1, wherein the pipeline card and the detector sub-array modules include printed circuit boards having conductive ground planes that cooperate to channel heat in the data measurement system and maintain substantial temperature uniformity through the data measurement system.

31. The data measurement system as set forth in claim 1, further including:

an optical slipring interface that optically transmits the data measurement system output from a rotating gantry on which the data measurement system is mounted to a stationary part of the computed tomography scanner.

32. A computed tomography method for imaging a subject, the computed tomography method comprising:

(a) transmitting x-rays through the subject;

(b) converting transmitted x-rays into analog electrical signals over a two-dimensional spatial surface;

(c) digitizing the analog electrical signals into digital signals;

(d) communicating the digital signals from across the two-dimensional spatial surface to a central location respective to the two-dimensional spatial surface via paired communication paths arranged symmetrically about the two-dimensional spatial surface;

(e) storing the digital signals arriving at the central location; (f) repeating the steps (a)–(e) for a plurality of orientations of the two-dimensional spatial surface; and (g) reconstructing the stored digital signals to generate an image representation of the subject.

33. The computed tomography method as set forth in claim 32, wherein the digitizing step (c) occurs over a spatial region that generally conforms with the two-dimensional spatial surface.

34. The computed tomography method as set forth in claim 32, wherein the converting step (b) includes:
   performing spatially localized conversions to produce local analog signals, wherein the spatial distribution of the spatially localized conversions defines the two-dimensional spatial surface.

35. The computed tomography method as set forth in claim 34, wherein the digitizing step (c) includes:
   for each spatially localized conversion, digitizing the corresponding local analog signal in close proximity to the spatially localized conversion.

36. The computed tomography method as set forth in claim 32, wherein the digitizing step (c) includes:
   multiplexing the digital signals into paired serial digital signals for communication via the paired communication paths.

37. A data measurement system for a computed tomography scanner, the data measurement system comprising:
   a mechanical frame having four symmetric quadrants defined by first and second planes of symmetry;
   a plurality of detector sub-array modules each including an x-ray detector sub-array, each detector sub-array module arranged symmetrically about the first plane of symmetry, the plurality of sub-array modules distributed across the mechanical frame symmetrically about the second plane of symmetry;
   four pipeline cards symmetrically arranged in the four symmetric quadrants, wherein each detector sub-array module electrically communicates with two pipeline cards; and
   a processor arranged at an intersection of the first and second planes of symmetry, the processor communicating with the pipeline cards to receive signals produced by the x-ray detector sub-arrays of the detector sub-array modules and processing the received signals for transmission off a rotating gantry on which the data measurement system is mounted.

38. The data measurement system as set forth in claim 37, wherein each detector sub-array module includes two electrical connectors arranged symmetrically about the first plane of symmetry, each electrical connector plugging into one of the pipeline cards.

39. The data measurement system as set forth in claim 37, wherein the mechanical frame includes:
   cradle support elements parallel to the first plane of symmetry; and
   crossing elements parallel to the second plane of symmetry and connecting the cradle support elements.

40. The data measurement system as set forth in claim 39, wherein the cradle support elements are constructed from plate metal, and the crossing elements are constructed from stock extrusions.

41. A data measurement method for a computed tomography scanner, the method comprising:
   with a plurality of connectorized detector sub-array modules, converting x-rays into electrical signals;
   transmitting the electrical signals by a signal connector;
   receiving the transmitted electrical signals with a pipeline card;
   with a processor, constructing a data measurement output from the electrical signals received by the pipeline card.

42. A method of assembling a data management system for a computed tomography scanner, the method comprising:
   mounting a plurality of detector sub-array modules on a mechanical frame having four symmetric quadrants defined by first and second planes of symmetry symmetrically about the first plane of symmetry and distributed across the mechanical frame along the second plane of symmetry;
   mounting pipeline cards in the four symmetric quadrants and connecting each pipeline card electrically to two pipeline cards;
   mounting a processor for transmitting signals off a rotating gantry at an intersection of the first and second planes of symmetry and connecting the processor electrically to the pipeline cards such that electrical signals from the detector sub-array modules are communicated to the processor for processing.

* * * * *